(12) United States Patent
Israelson

(10) Patent No.: US 8,809,417 B2
(45) Date of Patent: Aug. 19, 2014

(54) SOFT SHAPEABLE ADHESIVE PASTE

(75) Inventor: Dorrit Diana Israelson, Gentofte (DK)

(73) Assignee: Coloplast A/S, Humlebaek (DK)

( * ) Notice: Subject to any disclaimer, the term of this patent is extended or adjusted under 35 U.S.C. 154(b) by 364 days.

(21) Appl. No.: 13/140,289

(22) PCT Filed: Dec. 18, 2009

(86) PCT No.: PCT/DK2009/050345
§ 371 (c)(1),
(2), (4) Date: Jun. 16, 2011

(87) PCT Pub. No.: WO2010/069334
PCT Pub. Date: Jun. 24, 2010

(65) Prior Publication Data
US 2011/0251300 A1    Oct. 13, 2011

(30) Foreign Application Priority Data
Dec. 19, 2008 (DK) .................................. 2008 01820

(51) Int. Cl.
*A61F 5/443* (2006.01)
*C08L 31/04* (2006.01)
*C09J 131/04* (2006.01)

(52) U.S. Cl.
USPC .............. 523/105; 523/111; 525/88; 525/95; 524/505; 524/563; 604/344

(58) Field of Classification Search
CPC ..... A61L 15/58; A61L 15/585; A61L 26/008; A61L 24/0031; A61L 24/043
USPC ............. 523/105, 111; 524/505, 563; 525/88, 525/95; 604/344

See application file for complete search history.

(56) References Cited

U.S. PATENT DOCUMENTS

| 3,908,658 | A | | 9/1975 | Marsan |
| 4,191,673 | A | | 3/1980 | Wiesman |
| 4,855,335 | A | * | 8/1989 | Neperud .................. 523/111 |
| 6,184,285 | B1 | * | 2/2001 | Hatfield et al. ............... 524/505 |
| 8,394,896 | B2 | * | 3/2013 | Pazur et al. .................. 525/330.3 |
| 2003/0181586 | A1 | * | 9/2003 | Parg et al. ..................... 525/88 |
| 2006/0135694 | A1 | * | 6/2006 | Vaughan et al. ................ 525/88 |

FOREIGN PATENT DOCUMENTS

| DE | 147613 | 4/1981 |
| WO | WO 97/26306 | 7/1997 |
| WO | WO 98/17212 | 4/1998 |
| WO | WO 98/17329 | 4/1998 |
| WO | WO 02/066087 | 8/2002 |
| WO | WO 2009/006901 | 1/2009 |

OTHER PUBLICATIONS

Kraton® G1657 M Polymer Data Document; Kraton, Jul. 31, 2009.*

* cited by examiner

*Primary Examiner* — Michael Pepitone
(74) *Attorney, Agent, or Firm* — Coloplast Corp., Coloplast A/S; Nick Baumann

(57) ABSTRACT

The present invention relates to a pressure sensitive paste composition for skin application. The paste comprises 10-50% (w/w) based on the total paste formulation of a blend of polar polyethylene copolymer(s) and polar oil.

17 Claims, No Drawings

# SOFT SHAPEABLE ADHESIVE PASTE

This is a national stage of PCT/DK09/050,345 filed Dec. 18, 2009 and published in English, which claims the priority of Denmark number PA 2008 01820 filed Dec. 19, 2008, hereby incorporated by reference.

FIELD OF THE INVENTION

The invention relates to a soft and easy shapeable paste composition, which can be used for sealing between a stoma and a skin barrier. Furthermore, the composition can be used for smoothing out an irregular skin area for subsequent secure attachment of a skin barrier.

BACKGROUND OF THE INVENTION

In connection with surgery for a number of diseases in the gastro-intestinal tract a consequence is in many cases, that the colon, the ileum or the urethra has been exposed surgically. The patient is left with an abdominal stoma and the effluents or waste products of the body, which are conveyed through these organs, are discharged through the artificial orifice or opening and are collected in a collection bag. The bag is usually adhered to the skin by means of an adhesive wafer or plate having an inlet opening for accommodating the stoma.

Often a paste is used for filling an area between the stoma and the skin barrier in order to provide a safe seal, or building up an irregular abdominal skin area around the stoma to achieve a smooth surface onto which an appliance can be securely attached.

Such pastes should have a composition which makes it sufficiently tacky to attach safely to the skin on an immediate basis, easily shaped by finger pressure, and removable in one piece without leaving residues. Furthermore, the composition should be skin friendly, have a high moisture absorption level and a high erosion resistance in order not to expose the skin to exudates from the stoma.

Ostomy pastes are commercially available in the form of sticks/strips or rings, for example Coloplast ostomy paste, Eakin® ring, Stomahesive© paste marketed. International Publication No. WO 98/17329 describes a mouldable mass of hypoallergenic, substantially non-memory putty-like adhesive for use in connection with fistulas or ostomy appliances. The composition comprises 1-20 wt. % of a block copolymer having a major content of di-block copolymer, 5-60 wt. % of a tackifying liquid constituent and 1-10 wt. % of a waxy constituent.

Eakin Cohesive®, a hydrocolloid product available from TG Eakin Limited is said to be a mouldable, easily shaped, moisture absorbing skin barrier. According to information extracted from the Eakin website, http://www.eakin.co.uk, it can be stretched, compressed or moulded to fit the exact shape and size as required. Eakin Cohesive contains no active ingredients but is said to contain a unique carbohydrate which is slowly released while the seal is in place, diluting harmful enzymes, and protecting the skin against body wastes and fluids such as bile and ileal fluid. The product can be used as a seal under stoma pouches and appliances, as a packing agent in skin folds and scars, as a seal around drain tubes and fistulae, and as a "picture frame" around wound edges prior to dressing application.

These pastes suffer from two essential drawbacks:
1. In order not to remember its original shape (non-memory), the pastes have a high level of plasticity. However, after use it is desirable to be able to remove the pastes in one piece without leaving a large amount of, hard to cleanse, residues on the skin. For that reason a high volume of particles in the form of hydrocolloids are added not only in order to achieve the desired moisture absorption rate and capacity, but also to make the shape of the pastes stabile during use and minimise residue left on the skin after removal. The high volume of particles makes the paste harder, and for end-users it requires a certain amount of finger/hand strength. It is often time consuming to shape the pastes to fit the skin.
2. The pastes have high moisture absorptions in order to achieve optimum adhesive performance and maintain a healthy skin. However, the necessary absorption level combined with the level of plasticity needed for the pastes to be non-memory like, means that it will disintegrate easily due to the swelling of the hydrocolloids when in contact with exudates. The poor erosion resistance makes the service life short, promotes leakage and/or makes the skin of the users exposed to contact with aggressive output, leading to skin issues.

As a method of improving the erosion resistance of hydrocolloid adhesives the use of cross-linked hydrocolloids is described. Cross-linked hydrocolloids (for example carboxymethyl cellulose (CMC), dextrane) will not dissolve due to the cross-linked structure. During the swelling process, the individual particles will therefore obtain a gel like structure, but no coherent gel can be formed since molecules in the cross-linked materials are locked in a network constituting individual particles. However, in contact with exudates, the cross-linked hydrocolloids will be leached out due to the lack of a cohesive gel, and the effect on the erosion resistance is therefore limited.

Another method is increasing the cohesion of the continuous phase. Thereby the continuous phase will be less prone to disintegration during the swelling of the hydrocolloids. The drawback of utilising this method is that the increased cohesiveness will reduce the absorption rate, and ultimately a deficiency in plastic deformation will make the paste lose contact with the skin and exposing it, due to excessive swelling in the contact with exudates.

It has now surprisingly been found that by utilising a soft permeable composition, a paste can be produced that is easier to shape and has improved erosion resistance, without compromising the moisture absorption, ease of removal or introducing other possible adverse effects.

SUMMARY OF THE INVENTION

The present invention relates to a pressure sensitive paste composition for skin application. The paste comprises 10-50% (w/w) based on the total paste formulation of a blend of polar polyethylene copolymer(s) and polar oil.

DETAILED DESCRIPTION OF THE INVENTION

The soft permeable composition used is a polar polyethylene copolymer comprising a polar plasticizing oil such as described in International Patent Application No. WO2009/006901. The compositions described in International Patent Application No. WO2009/006901 are hot melt processable comprising more than 10% (w/w) of polar plasticizing oil and a content of 10-50% of polyethylene copolymer(s) with a melt flow index below 2 g/10 min (190° C./21.1N).

These soft permeable compositions are themselves not suited for preparing an ostomy paste due to the high molecular weight of the polyethylene vinyl copolymers. A paste made entirely of these materials would either have to be so soft that it would be impossible to handle during use, or it will have too high a level of elastic properties for a paste to sustain` the desired form after the shaping procedure. However, when these materials are mixed with traditional paste compositions, favourable rheological properties are surprisingly achieved.

In one embodiment of the invention, the pressure sensitive paste composition for skin application comprises 10-50% (w/w) based on the total paste formulation of a blend of polar polyethylene copolymer(s) and polar oil.

By introducing a soft highly permeable polyethylene copolymer composition in the otherwise non-permeable continuous phase it is possible to achieve a softer paste either by using a lower amount of hydrocolloids and/or by increasing the cohesiveness and softness of the paste without lowering moisture absorption rate or introducing the failure modes that are normally related to the elastic properties of the paste (tensions in the shaped paste, excessive swelling in contact with body fluids).

For the end-user, these improvements mean that it is much easier (or possible) to shape the paste to the desired form. Some users could possibly do the shaping directly on the abdominal skin, thereby achieving a safer seal between the stoma and the adhesive base plate or a more secure attachment of the base plate over skin irregularities. The increased erosion resistance of the pastes will also add to the safety of the users, as erosion often promotes leakage. Furthermore, skin contact with aggressive body exudates has proven to be the major cause of skin problems for people with an ostomy. The erosion resistance of this new type of paste will significantly minimise the exposure of the peristomal skin during use, and help maintain a healthy skin.

Combining thermoplastic materials that are highly permeable and non-polar materials (continuous phase) respectively, could cause stability issues due to phase separation or migration. However, ageing studies have proven that these compositions according to the invention have the desired stability with respect to water absorption, adhesion and rheological properties. Dynamic mechanical analysis shows uniform curves of $|G^*|$ and tan($\delta$) with a combined rheological expression of both the non-polar and the highly permeable part.

In one embodiment of the present invention, the blend of polar polyethylene copolymer(s) and polar oil comprises a polar plasticizing oil or a combination of polar plasticizing oils in the content of above 10% (w/w) of the blend, the content of the polyethylene copolymer(s) is 10-50% (w/w) of the blend, and at least one polar polyethylene copolymer has a melt flow index below 2 g/10 min (190° C./21.1N).

The blend may be mixed with any conventional paste or mouldable adhesive such as the ones described in International Publication Nos. WO 98/17329 and WO 98/17212.

In another embodiment of the present invention, the blend of polar polyethylene copolymer(s) and polar oil comprises a polar plasticizing oil or a combination of polar plasticizing oils in the content of above 10% (w/w) of the blend, the content of the polyethylene copolymer(s) is 10-50% (w/w) of the blend, and the polar polyethylene copolymer(s) has a melt flow index below 2 g/10 min (190° C./21.1N).

In an embodiment of the invention, the final paste in continuous form exhibits a moisture vapour transmission rate of at least 150 g/m$^2$/24 hours, preferably at least 200 g/m$^2$/24 hours for a 1 mm sheet when measured according to MVTR test method.

According to one embodiment of the invention, the final paste has a complex modulus $|G^*|$ of less than 1,000,000 Pa, preferably less than 250,000 Pa at 1 Hz (1% deformation, 32° C.).

According to one embodiment of the invention, the final paste has a tan($\delta$) above 0.9, preferably above 1.0 at 1 Hz (1% deformation, 32° C.).

The primary polymers used in the blend are polyethylene copolymers. The copolymer should contain a considerable amount of a polar component to get high water permeability.

In one embodiment of the invention, the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

The polar polyethylene copolymer is preferably ethylene vinyl acetate.

By polar polymers is meant polymers with water transmission above 50 g/m$^2$/day for a 150 μm film when measured according to the MVTR test method.

In an embodiment of the invention, the ethylene vinyl acetate has a content of at least 40% (w/w) vinyl acetate preferably with 40-80% (w/w) vinyl acetate.

Preferably, the polar polyethylene copolymers used in the paste should have a molecular structure at a level that results in a melt flow index (MFI) below 2 g/10 min (190° C./21.1N). The melt flow index can be measured by the methods given in ISO 1133 and ASTM D1238.

The advantage of using a polymer with high molecular weight and low MFI is that the high molecular weight polymer can ensure a sufficient high cohesive strength to the paste.

By the content of the final paste is meant the percentage in weight of the ingredient in relation to the total weight of the ingredients used in the paste composition.

In an embodiment of the invention, the content of the polar polyethylene copolymer(s) is 5-20% (w/w) of the final paste.

In another embodiment of the invention, the polar polyethylene copolymer(s) has a molecular weight above 250,000 g/mol.

In one embodiment of the present invention, the paste composition comprising a polar plasticizing oil or a combination of polar plasticizing oils in the content of 5-40% (w/w) of the final paste.

In one embodiment of the present invention, the paste composition comprising a polar plasticizing oil wherein the polar plasticizing oil is selected from the group of liquid rosin derivatives, aromatic olefin oligomers, vegetable and animal oils and derivatives. Preferable polar oils are esters, ethers and glycols.

Particularly preferable oils are poly propylene oxides such as alpha-butoxy-polyoxypropylene. Polypropylene oxide oil contributes to a high permeability of the paste composition.

Some of the paste compositions according to the invention contain a minor amount of additional polar polymer in the blend besides the main polymer adding cohesion. This or these additional polymers are added to give tack. These additional polymers are optional and not necessary for all purposes.

In one embodiment of the invention, the paste composition further comprises a low molecular weight polar polymer, that is MFI>2.

The addition of a low Mw polymer to the paste may be an advantage when a lot of moisture is present between the paste and the skin.

Additional components may be added to the composition such as tackifier resin.

In one embodiment of the invention, the paste composition further comprises a tackifier resin such as natural, modified or synthetic resins preferably polar resins such as rosins, rosin esters, hydrogenated rosins, hydrogenated rosin esters, and derivatives of such polar resins or pure aromatic monomer resins.

Tackifier resins can be added to control tack in the paste, that is reduce moduli and increase glass transition temperature.

The content of the tackifier resin is 0-20% (w/w) of the final paste. Preferably the paste is substantially free of resin. When the paste composition contains resin, the content of the tackifier resin is preferably 0.1-20% (w/w) of the final paste.

In another embodiment of the invention, the paste composition further comprises other ingredients selected from the group of antioxidants, stabilisers, fillers, pigments, flow modifiers, and active ingredients.

In one preferred embodiment of the invention, the paste composition comprises polar active ingredients.

According to an embodiment of the invention, the composition further comprises absorbing particles such as hydrocolloid.

As with traditional hydrocolloid adhesives and pastes, most liquid absorbing polymeric particles can be used, including microcolloids.

More particularly, the hydrocolloids may be guar gum, locust bean gum (LBG), pectin, alginates, potato starch, gelatine, xanthan, gum karaya; cellulose derivatives (e.g. salts of carboxymethylcellulose such as sodiumcarboxymethylcellulose, methylcellulose, hydroxyethyl cellulose and hydroxypropylmethylcellulose), sodium starch glycolate, polyvinylalcohol and/or polyethylene glycol.

In one embodiment of the invention, the content of hydrocolloid is 20-60% (w/w) of the total composition.

Microcolloid particles are well known in the art, for example from International Publication No. WO 02/066087, which discloses adhesive compositions comprising microcolloid particles. The microcolloid particles may have a particle size of less than 20 microns.

In one embodiment of the invention, the pressure sensitive paste composition comprises based on the total formulation 1-10% (w/w) of a blockcopolymer having a major content of di-block, 10-35% (w/w) of a tackifying liquid constituent, and 1-8% (w/w) of a waxy constituent.

By a major content of di-block is meant that the content of di-block in the blockcopolymer is above 25% (w/w), preferably above 30% (w/w), and more preferably above 50% (w/w) of the total amount of blockcopolymer.

According to one embodiment of the invention, the pressure sensitive paste composition comprises, based on the total formulation 1-10% (w/w) of a blockcopolymer having a content of di-block above 30%, 10-35% (w/w) of a tackifying liquid constituent, and 1-8% (w/w) of a waxy constituent.

According to an embodiment of the invention, the pressure sensitive paste composition comprises, based on the total formulation 5-25% (w/w) polar polyethylene copolymer, 5-40% (w/w), of a polar oil, 1-10% (w/w) of a blockcopolymer having a major content of di-block, 10-35% (w/w) of a tackifying liquid constituent, 1-8% (w/w) of a waxy constituent, and 20-60% (w/w) hydrocolloids.

The blockcopolymer may be a copolymer comprising a block of a relatively hard polymer which may form physical cross-linking and a block of a softer polymer. The constituents of the blockcopolymer may be the same as are conventionally used for blockcopolymers such as SBS, SIS or SEBS copolymers, for example styrene and butadiene, isoprene or ethylenebutylene copolymers. The preferred copolymer is a styrene-ethylenebutylene-styrene copolymer (SEBS) having a content of di-block component above 30%.

The tackifying viscous liquid constituent is preferably a viscous polymeric material being compatible with the blockcopolymer. The tackifying liquid may be a polybutylene or polyisobutylene. The molecular weight of a tackifying viscous polymeric component is preferably from 10,000 to 120,000 when determined by GPC.

The waxy component may for example be a mineral wax or petroleum jelly, however, preferably a microcrystalline wax that is compatible with the preferred block copolymer SEBS.

The invention also relates to medical devices comprising a pressure sensitive paste composition as described above.

The medical device comprising a paste composition according to the invention may be an ostomy appliance, a device for collecting urine or a faecal management device.

EXPERIMENTAL

Laboratory Methods

Method 1: Mixing

The adhesives were compounded in an Aoustin mixer MX 0.4 (contains about 200 grams), from F. Aoustin et Cie, 11 Rue de Préaux 76161 Darnetal, France.

The chamber temperature in the mixer was approx. 90° C. and the adhesive was compounded with 30-45 rpm.

Premix of the polar polyethylene copolymer and oil was added to the mixer together with extra PPO, premix 2 and hydrocolloids. The compound was mixed for approx 30 min.

Method 2: Mechanical Degradation of Pre-Cross-Linked Levamelt

In some cases, it was necessary to perform a mechanical degradation of the pre-cross-linked EVA, for example when Levamelt 500 was used. The polymer was mixed for about 10 hours in a cold Hermann Linden LK II 0.5 mixer to get mechanical breakdown of the polymer chains. The heating system was not turned on and the mixing speed kept low, app. 20 rpm, to ensure optimal mechanical work on the polymer. The breakdown of the polymer was followed by visual inspection of a thermoformed film of the treated polymer. The mechanical treatment was continued until only a minor amount of polymer gel-lumps remained.

Method 3: Gamma Irradiation 1 kilo of the polymer was placed in a plastic bag. The bag was packed and sent to the gamma irradiation supplier, for example BGS Beta-Gamma Service, Wiehl, Germany. The polymer was irradiated with the specified gamma dose, for example 30 kGy. The gamma radiation increases the molar weight of the polymer. When the polymer was returned, it was mixed with oil, to obtain pre-mixtures as described above.

Method 4: Determination of Moisture Absorption

Samples were prepared by thermoformed to an approx. 1±0.1 mm adhesive film between two release liners.

With a punching tool, samples were punched out. Sample size was 25×25 mm. The release liners were removed. The samples were glued to an object glass and placed in a beaker with physiological salt water and placed in an incubator at 37° C.

Calculation:

The sample was weighed over time (=M(10 min)).

For a 25×25 mm sample the area was 6.25 cm² (the surface edges were left out of the area).

The moisture absorption may be calculated as:

$$\text{water abs. after 2 hours} = \frac{M(2 \text{ hours}) - M(\text{start})}{6,25} \ [\text{g/cm}^2]$$

Method 5: Determination of Moisture Vapour Transmission Rate (MVTR)

MVTR was measured in grams per square meter (g/m$^2$) over a 24 hour period using an inverted cup method.

A container or cup that was water and water vapour impermeable having an opening was used. 20 ml saline water (0.9% NaCl in demineralised water) was placed in the container, and the opening was sealed with the test adhesive film. The container was placed into an electrically heated humidity cabinet, and the container or cup was placed upside down such that the water was in contact with the adhesive. The cabinet was maintained at 37° C. and 15% relative humidity (RH). The weight loss of the container was followed as a function of time. The weight loss was due to evaporation of water vapour transmitted through the adhesive film. This difference was used to calculate Moisture vapour transmission rate or MVTR. MVTR was calculated as the weight loss per time divided by the area of the opening in the cup (g/m$^2$/24 h). The MVTR of a material was a linear function of the thickness of the material. Thus, when reporting MVTR to characterise a material, it was important to inform the thickness of the material which MVTR was reported. We used 1.0 mm as a reference. If thinner or thicker samples were measured, the MVTR was reported as corresponding to a 1.0 mm sample.

Finally, we noted that by using this method, we introduced an error by using a supporting PU film. The error was eliminated by utilising the fact that the adhesive/film laminate was a system of two resistances in series. When the film and the adhesive were homogeneous, the transmission rate may be expressed as:

$$1/P(\text{measured}) = 1/P(\text{Film}) + 1/P(\text{Adhesive})$$

Hence, by knowing the film permeability and thickness of the adhesive, it was possible to calculate the true permeability of the adhesive (P(Adhesive)) using the following expression:

$$P(\text{adhesive}) = d(\text{Adhesive})/150\ \text{micron} * 1/(1/P(\text{measured}) - 1/P(\text{Film}))$$

where d(Adhesive) was the actual measured thickness of the adhesive and P(Film) was the MVTR of the film with no adhesive, and P(measured) was the actual measured MVTR.

Method 6: Determination of Erosion Resistance

Samples were prepared by thermoforming a 2±0.1 mm adhesive plate between two release liners. Said adhesive plate was transferred and laminated with a non-permeable foil on both sides.

With a punching tool round samples were punched out and placed in closed beakers with physiological salt water and placed at room temperature (23° C.). The beakers were rotated to obtain dynamical mechanical stress of the sample at the same time as water absorption took place.

After 18 hours the eroded part was measured in mm in radial direction from the centre hole towards the outer periphery of the sample.

Method 7: Determination of Peel Failure Mode:

Peel failure mode was determined by peeling the sample from skin.

Peel failure mode, that is adhesive or cohesive failure of the adhesive, was visually observed. Cohesive failure was unwanted, as adhesives with cohesive failure were likely to leave residues on the substrate when removed.

The test samples were prepared by thermoforming an approximately 1±0.1 mm adhesive film between two release liners. Said adhesive film was transfer coated onto a 30 μm polyurethane film.

The test specimens were applied to the underside of the forearm and left for about 2 hours before they were peeled. The results were reported as Adhesive or Cohesive peel failure mode.

Method 8: Dynamic Mechanical Analysis (DMA) and Determination of G' and tan(δ)

The parameters |G*| and tan(δ) were measured as follows: The adhesives were pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurements were carried out at 32° C.

Materials

| Name | Chemistry | Supplier |
|---|---|---|
| SIS Kraton G 1726 x | Styrene block copolymer | Kraton Polymer |
| Indopol H-18000 | Polybutene | AWL Kemi Aps |
| Eastoflex | Amorf polyolefin | Brøste |
| Sasol micro wax | PE-wax | Sasol wax |
| Levamelt 700 | Ethylene vinyl acetate copolymer | Lanxess |
| Levamelt 500 | Ethylene vinyl acetate copolymer | Lanxess |
| Polyglycol B01/120 | Poly Propylene oxide oil | Clariant |
| Natrosol 250HX Pharma | Hydrocolloids | Hercules |
| Pektin Pomosin LM 12 | Hydrocolloids | CP Kelco Aps |
| Guar Gum | Hydrocolloids | Nordisk Gelatine |
| Gelatin | Hydrocolloids | PB Gelatines |
| Zink oxide | Colourant | Harcros Chemicals Inc |

| Pre-mix 2 Raw material | [%(w/w)] |
|---|---|
| Kraton G 1726 X | 12.5 |
| Indopol H-18000 | 75 |
| Eastoflex | 6.25 |
| Sasol micro wax | 6.25 |
| Total: | 100.00 |

Table pre-mix strip paste [%(w/w)]

Results

Example 1

Measured according to method 4, 5, 6, 7 and 8:
Moisture absorption, moisture vapour transmission rate (MVTR), erosion resistance, peel failure mode and DMA.

| Sample number | 065.01 | 065.02 | #10 | #11.B | #12 | #13 | #14 | #15 | #27 |
|---|---|---|---|---|---|---|---|---|---|
| Pre-mix 2 | 27 | 21.5 | 30 | 28.9 | 28.5 | 28.5 | 27 | 63.5 | 30.25 |
| Levamelt 700, 22KGy | 15 | 15 | 11 | 10.5 | 9.75 | 9.75 | 10.25 | | 12.8 |

-continued

| Sample number | 065.01 | 065.02 | #10 | #11.B | #12 | #13 | #14 | #15 | #27 |
|---|---|---|---|---|---|---|---|---|---|
| Levamelt 500, 17KGy | | | | | 2 | 1.5 | 1.5 | | |
| Clariant B01/120 Polyglycol | 24.0 | 29.5 | 22.5 | 21.6 | 23.25 | 23.75 | 20.75 | | 21.7 |
| Total | 66 | 66 | 63.5 | 61 | 63.5 | 63.5 | 59.5 | 63.5 | 64.75 |
| Natrosol 250HX Pharm | | | 13 | 12.5 | 13 | 13 | 13 | 13 | 9 |
| Pektin Pomosin LM 12 Cg-Z/200 | 14 | 14 | 11.5 | 11 | 11.5 | 11.5 | 14.5 | 11.5 | 12 |
| Guar Gum | | | 3 | 3 | 3 | 3 | 3 | 3 | |
| Gelatine | 20 | 20 | 8.5 | 12 | 8.5 | 8.5 | 9.5 | 8.5 | 14.25 |
| Potato starch | | | | | | | | | |
| ZnOx | | | 0.5 | 0.5 | 0.5 | 0.5 | 0.5 | 0.5 | |
| Total, hydrocolloid | 34 | 34 | 36.5 | 39 | 36.5 | 36.5 | 40.5 | 36.5 | 35.25 |
| Moisture absorbance, 2 hours g/cm$^2$ | 0.026 | 0.036 | 0.14 | 0.13 | 0.15 | 0.15 | 0.15 | 0.16 | 0.13 |
| Transmission, 1 mm sample, g/m$^2$/day | 462 | 682 | | | | 695 | | 90 | |
| Erosion, borderline, mm | 0 | 0 | 0.2 | 0.2 | 0 | 0 | 0 | 3 | 0 |
| Peel failure mode | Adhesive | Cohesive | Cohesive | Cohesive | Adhesive | Adhesive | Adhesive | Cohesive | Adhesive |
| DMA, module \|G*\| tan delta, 1 Hz | 8.87e+04 0.98 | 6.74e+04 0.97 | 8.96e+04 1.17 | 7.57e+04 1.17 | 1.15e+05 0.93 | 1.05e+05 1.03 | 1.31e+05 0.97 | 2.69e+05 1.88 | 1.2e+05 1.0 |

The polar polyethylene copolymer/PPO oil premixes are softer but more elastic than the non-polar Pre-mix 2. Therefore, composition #10 to #14 & #27 show a higher elasticity but a decrease in hardness with increased addition of the polar premixes as compared to #15 that only contains the non-polar Pre-mix 2.

It can also be observed that the polar polyethylene copolymer and polar plasticizing oil compounded with the more plastic non-polar Pre-mix 2, results in more elastic compositions with low erosion and without compromising the moisture absorption level due to the increased vapour transmission.

The DMA results and Peel failure mode tests show that it is possible to produce a paste with optimal adhesion and easy adaptability to skin irregularities and -folds and sufficient cohesive strength for subsequent removing in one piece, such as #10-15 & 27 (adhesive peel failure).

Compositions of Levamelt and PPO Oil with Pre-Mix 2

| Sample number | 066.01 | 066.02 | 066.04 | 066.06 | #14 | #27 |
|---|---|---|---|---|---|---|
| Pre-mix 2 | 37 | 17 | 17 | 17 | 27 | 30.25 |
| Levamelt 700, 22KGy | 8.15 | 15.4 | | | 20.5 | 12.8 |
| Levamelt 500, 17KGy | | | 42.5 | | 3 | |
| Clariant B01/120 Polyglycol | 14.35 | 27.1 | | 21.3 | 9 | 21.7 |
| Levamelt 700 | | | | 21.3 | | |
| Total | 59.5 | 59.5 | 59.5 | 59.6 | 59.5 | 64.75 |
| Natrosol 250HX Pharm | 13 | 13 | 13 | 13 | 13 | 9 |
| Pektin Pomosin LM 12 Cg-Z/200 | 14.5 | 14.5 | 14.5 | 14.5 | 14.5 | 12 |
| Guar Gum | 3 | 3 | 3 | 3 | 3 | |
| Gelatine | 9.5 | 9.5 | 9.5 | 9.5 | 9.5 | 14.25 |
| Potato starch | | | | | | |
| ZnOx | 0.5 | 0.5 | 0.5 | 0.5 | 0.5 | |
| Total, hydrocolloids | 40.5 | 40.5 | 40.5 | 40.5 | 40.5 | 35.25 |
| Transmission, 1 mm sample, g/m$^2$/day | 587 | 814 | | | | |

-continued

| Sample number | 066.01 | 066.02 | 066.04 | 066.06 | #14 | #27 |
|---|---|---|---|---|---|---|
| Peel failure mode | Adhesive | Adhesive | Adhesive | Adhesive | Adhesive | Adhesive |
| DMA, module G*, tan delta, 1Hz, | 2.07e+05, 0.99 | 1.16e+05, 0.80 | 7.62e+05, 0.54 | 2.64e+05, 0.87 | 1.15e+05, 0.93 | 1.2e+05 1.0 |

For 066.02, 0.04 and 0.06 the deformation of the paste will not be permanent due to the high level of elasticity.

066.01, #14 & #27 have however proven to work well as a paste. They are easy to shape by finger pressure and can easily build up an irregular abdominal skin area, and can be used for joining a skin barrier to irregular abdominal skin.

The invention claimed is:

1. A pressure sensitive paste composition for skin application comprising
   a) 10-50% (w/w) based on the total paste formulation of a blend of (i) polar polyethylene vinyl acetate copolymer(s) having a 40-80% (w/w) vinyl acetate content and (ii) polar poly propylene oxide oil,
   b) 1-10% (w/w) of a block copolymer having above 25% (w/w) di-block content, and
   c) 20-60% (w/w) hydrocolloids.

2. The pressure sensitive paste composition according to claim 1, wherein the polar propylene oxide oil constitutes above 10% (w/w) of the blend, the polyethylene vinyl acetate copolymer(s) constitutes 10-50% (w/w) of the blend, and at least one polar polyethylene vinyl acetate copolymer has a melt flow index below 2 g/10 min (190° C./21.1N).

3. The pressure sensitive paste composition according to claim 1 in continuous form exhibiting a moisture vapour transmission rate of at least 150 g/m2/24 hours for a 1 mm sheet when measured according to the MVTR test method.

4. The pressure sensitive paste composition according to claim 1 having a complex modulus |G*| of less than 1,000,000 Pa at 1 Hz (1% deformation, 32° C.).

5. The pressure sensitive paste composition according to claim 1 having a tan(δ) above 0.9 at 1 Hz (1% deformation, 32° C.).

6. The pressure sensitive paste composition according to claim 1, wherein the content of the polar polyethylene vinyl acetate copolymer(s) is 5-20% (w/w) of the paste.

7. The pressure sensitive paste composition according to claim 1, wherein the polar polyethylene vinyl acetate copolymer(s) has a molecular weight of above 250,000 g/mol.

8. The pressure sensitive paste composition according to claim 1, wherein the polar poly propylene oxide oil is alpha-butoxy-polyoxypropylene.

9. The pressure sensitive paste composition according to claim 1, wherein the ratio of polar polyethylene vinyl acetate copolymer to polar poly propylene oxide oil is between 1:1 and 1:3.

10. The pressure sensitive paste composition according to claim 1 comprising a polar polymer having a MFI>2 (190° C./21.1N).

11. The pressure sensitive paste composition according to claim 1 comprising a tackifier resin.

12. The pressure sensitive paste composition according to claim 11, wherein the content of the tackifier resin is 0.1-20% (w/w) of the paste.

13. The pressure sensitive paste composition according to claim 1, wherein the composition further comprises other ingredients selected from the group consisting of antioxidants, stabilisers, fillers, pigments, flow modifiers, and active ingredients.

14. The pressure sensitive paste composition according to claim 1 further comprising, based on the total paste formulation, 1-10% (w/w) of a block copolymer having a major content of di-block, 10-35% (w/w) of a tackifying liquid constituent, and 1-8% (w/w) of a waxy constituent.

15. The pressure sensitive paste composition according to claim 1 further comprising, based on the total paste formulation, 5-25% (w/w) polar polyethylene vinyl acetate copolymer, 5-40% (w/w) of a polar poly propylene oxide oil, 1-10% (w/w) of a block copolymer having a major content of di-block, 10-35% (w/w) of a tackifying liquid constituent, 1-8% (w/w) of a waxy constituent, and 20-60% (w/w) hydrocolloids.

16. A medical device comprising a pressure sensitive paste composition according to claim 1.

17. The medical device according to claim 16, wherein the medical device is an ostomy appliance, a urine collecting device or a faecal management device.

* * * * *